United States Patent [19]

Komp et al.

[11] Patent Number: 5,098,694

[45] Date of Patent: Mar. 24, 1992

[54] NATURAL DEODORANT COMPOSITIONS

[75] Inventors: Bernd Komp, Seligenstadt; Christiane Gigengack, Reinheim, both of Fed. Rep. of Germany

[73] Assignee: The Procter & Gamble Company, Cincinnati, Ohio

[21] Appl. No.: 589,131

[22] Filed: Sep. 25, 1990

[51] Int. Cl.$^5$ .......... A61K 7/32; A61K 7/42; A61K 9/10; A61K 9/12

[52] U.S. Cl. ............... 424/47; 424/DIG. 5; 424/59; 424/65; 514/938; 514/941

[58] Field of Search .............. 424/65, 47; 514/847

[56] References Cited

U.S. PATENT DOCUMENTS

| | | | |
|---|---|---|---|
| 2,865,859 | 2/1958 | Lubowe | 424/65 |
| 3,725,540 | 4/1973 | Wahl | 424/47 |
| 4,010,253 | 3/1977 | Reese | 424/47 |
| 4,089,942 | 5/1978 | Bore | 424/47 |
| 4,508,705 | 4/1985 | Chaudhuri et al. | 424/65 |
| 4,777,034 | 6/1988 | Olivier | 424/65 |
| 4,832,945 | 5/1989 | Osipow et al. | 424/68 |
| 4,921,694 | 5/1990 | Hoppe et al. | 424/65 |

FOREIGN PATENT DOCUMENTS

| | | | |
|---|---|---|---|
| 2826757 | 12/1979 | Fed. Rep. of Germany | 424/65 |
| 2826758 | 12/1979 | Fed. Rep. of Germany | 424/65 |

OTHER PUBLICATIONS

The Merck Index, 1976, 9th Edition, pp. 142, 143 and 1126.

*Primary Examiner*—Dale R. Ore
*Attorney, Agent, or Firm*—John M. Howell; Steven J. Goldstein; Richard C. Witte

[57] ABSTRACT

A natural deodorant composition containing glyceryl laurate, sorbic or benzoic acid and citric acid.

16 Claims, No Drawings

NATURAL DEODORANT COMPOSITIONS

TECHNICAL FIELD

The field of the invention relates to deodorant compositions and a method of suppressing body odor using these compositions.

BACKGROUND OF THE INVENTION

Human perspiration is initially odorless but upon standing develops an unpleasant odor which is due almost entirely to bacterial decomposition of the perspiration. Cosmetic compositions designed to treat perspiration odor are generally designed to either eliminate perspiration odor or inhibit the flow of perspiration.

Cosmetic preparations which act by inhibiting the flow of perspiration are antiperspirants. Antiperspirants contain substances such as metal salts which inhibit perspiration flow due to their astringent properties. While antiperspirants are effective in eliminating perspiration, they often cause discoloration of clothes, skin irritation, or toxicity.

Cosmetic products which act by eliminating perspiration odor are known as deodorants. Deodorants generally do not alter the volume of perspiration secreted. Since most body odor is the result of bacterial action on perspiration, a satisfactory deodorant product must contain an effective antibacterial agent. phenolic derivatives, quaternary ammonium compounds, hexachlorophene, and certain ion exchange resins are known to be effective antibacterials and are used often in deodorants. However, bactericidal agents used in deodorants also exhibit undesireable properties because they totally destroy the microbial flora of the skin, disturbing biological equilibrium.

For example, Triclosan, which is a phenolic ether, has been widely used in deodorant compositions because of its excellent antibacterial properties. However, Triclosan exhibits certain undesireable properties and is particularly unpopular in Germany and other European countries because it is believed to contain traces of dioxines and furanes which are very environmentally undesireable and questionably safe for human use. There is thus a need for a deodorant composition which effectively inhibits body odor but without causing skin irritation or other undesireable effects.

SUMMARY OF THE INVENTION

The invention is directed to a deodorant composition comprising an odor suppressing effective amount of a combination of glyceryl laurate, sorbic or benzoic acid, and citric acid.

The invention is also directed to a method of suppressing body odor comprising applying the deodorant composition of the invention to the bodily area where odor suppression is desired.

DETAILED DESCRIPTION

The essential, active ingredients of the deodorant composition are an odor suppressing effective amount of the combination of glyceryl laurate, sorbic acid or benzoic acid, and citric acid.

Glyceryl laurate (also known as glyceryl monolaurate) is the monoester of glycerin and lauric acid. Glyceryl laurate is widely available from many commercial sources. An odor suppressing effective amount of glyceryl laurate in accordance with the invention generally ranges from 0.5–5%. The permissible range of glyceryl laurate is 0.5–3% and the preferred range of this essential constituent is 0.5–1.5%.

The second essential constituent of the composition is sorbic acid or benzoic acid, both of which are available from a number of commercial sources. An odor suppressing effective amount is about 0.1–0.5%. A permissible range of sorbic acid is 0.2–0.4% and the preferred range is 0.2–0.3%.

The final essential constituent of the composition is citric acid. Citric acid is also well known and widely available. An odor suppressing effective amount of citric acid is generally 0.1–0.5%. A permissible range of citric acid is 0.45–0.35% and the preferred range is 0.16–0.26%.

These three ingredients form the active complex. This active complex is utilized in conjunction with an aqueous/alcoholic carrier resulting in a deodorant composition with excellent odor suppressing properties.

The aqueous/alcoholic carrier ideally contains other ingredients such as solvents, emollients, humectants, salts, and fatty compounds. The aqueous/alcoholic carrier may also contain preservatives, colorants, fragrances, solubilizers, other stabilizers, etc. For example deodorants which contain specific colors or fragrances may be more desireable or commercially popular. Various humectants such as polyols, and emollients may be added to counteract skin irritation. Also, it may be desireable to add certain solvents to achieve desired properties.

Suitable solvents include alcohols such as ethanol (all SD alcohols with different denaturing agents), isopropanol (in all cosmetic or pharmaceutical grades) in mixtures with polyols such as propylene-, butylene-, hexyleneglycol, sorbitol, glycerol, polyethylene glycol.

A wide variety of emollients are suitable including but not limited to PPG-15 stearyl ether, PPG-5 Laureth 5, PPG-11 stearyl ether, PPG-3 myreth-3, PPG-3 myristyl ether or other propoxylated/ethoxylated fatty alcohol ethers.

Suitable salts are potassium hydroxide, sodium hydroxide, and potassium-, sodium-, ammonium carbonate, or ammonium hydroxide.

preservatives such as parabens, and stabilizers such as antioxidants and UV-filter substances e.g. benzophenones or thickeners such as hydroxypropylcellulose may be added.

Any of the FD&C and D&C colors are suitable as well as art recognized fragrances.

The preferred embodiment of the invention is a deodorant composition containing sorbic acid and wherein the aqueous/alcoholic carrier contains solvents, humectants, emollients, salts, fragrance, color, and U.V. stabilizers. If these optional ingredients are added to the aqueous carrier the following general ranges are suggested:
about 20–80.0% alcohol,
about 0.1–50.0% water,
about 0.1–40.0% humectant/solvent
about 0.05–0.5% salt If desired, the following ranges of fragrance and emollient may be added:
up to 5.0% fragrance
about 2.0–10.0% emollient The preferred embodiment of the invention is a deodorant composition comprising:
40–70% alcohol, particularly SD Alcohol 39-C
10–40% water, preferably purified water 5-20% butylene glycol
3-7% emollients (PPG-15 stearyl ether or PPG-5 Laureth 5) 0.1-3% fragrance
0 5-3% glyceryl laurate
0.2-0.4% sorbic acid
0.1-0.25% potassium hydroxide
0.15-0.35% citric acid Most preferably the composition comprises:
45-50% SD-alcohol 39-C
30-38% purified water
5-10% butylene glycol
4-6% PPG-15 stearyl ether or PPG-5 Laureth 5
0 1-2% fragrance
0.5-1.5% glyceryl laurate
0.2-0.3% sorbic acid
0.1-0.2% potassium hydroxide
0.16-0.26% citric acid The composition of the invention is made by simply mixing together the appropriate ingredients in the usual manner and placing the composition in the desired vehicle for administration.

The invention is also directed to a method for suppressing body odor comprising applying the deodorant composition of the invention to the bodily area where odor suppression is desired. For example, the composition may be applied once a day in the morning after washing or applied more than once a day if desired. The deodorant composition of the invention will suppress body odor for up to 6 to 8 hours. The composition is easily incorporated into spray containers such as pump sprays or aerosols, which allow the deodorant to be easily sprayed onto the desired area. Also roll-ons (clear or emulsion), sticks, or creams are suitable, however a pump spray container is preferred. The deodorant of the invention exhibits excellent odor suppression properties without using Triclosan, and does not cause the irritation often found with other commercial preparations.

The invention will be described in connection with the following examples which are set forth for the purpose of illustration only.

EXAMPLE 1

A deodorant composition was made as set forth below:

|  | W/W % |
| --- | --- |
| PEG-40 Hydrogenated Castor Oil | 1.000 |
| SD Alcohol 39-C | 46.750 |
| Purified water | 34.034 |
| Butylene glycol | 10.000 |
| PPG-15 stearyl ether | 5.000 |
| Fragrance | 1.500 |
| Glyceryl laurate | 1.000 |
| Sorbic acid | 0.224 |
| Potassium hydroxide (85%) | 0.132 |
| Citric acid | 0.180 |
| Benzophenone-2 | 0.100 |
| FD&C Blue no. 1 (aqueous solution 0.1%) | 0.080 |
|  | 100.00 |

EXAMPLE 2

The following formulation was made for use with a pump spray:

|  | W/W % |
| --- | --- |
| SD Alcohol 39-C | 46.750 |
| Purified water | 36.274 |
| Butylene glycol | 10.000 |
| PPG-5 Laureth-5 | 4.000 |
| Fragrance | 1.000 |
| Glyceryl Laurate | 1.000 |
| Sorbic acid | 0.224 |
| Potassium hydroxide (85%) | 0.132 |
| Citric acid | 0.240 |
| Benzophenone-2 | 0.200 |
| FD&C Yellow No. 6* | 0.100 |
| FD&C Yellow No. 5* | 0.080 |
|  | 100.00 |

*aqueous solution 0.1%

EXAMPLE 3

The following formulation was made for a roll-on deodorant:

|  | W/W % |
| --- | --- |
| SD Alcohol 39-C | 46.750 |
| Purified water | 35.854 |
| Butylene glycol | 10.000 |
| PPG-15 stearyl ether | 4.000 |
| Fragrance | 1.000 |
| Glyceryl laurate | 1.000 |
| PEG-40 hydrogenated castor oil | 0.400 |
| Hydroxypropylcellulose | 0.400 |
| Citric acid | 0.240 |
| Sorbic acid | 0.224 |
| Potassium hydroxide (85%) | 0.132 |
|  | 100.00 |

EXAMPLE 4

The following formulation was prepared for a roll-on

|  | W/W % |
| --- | --- |
| SD Alcohol 39-C | 46.750 |
| Purified water | 35.504 |
| Butylene glycol | 10.000 |
| PPG-5 Laureth 5 | 4.000 |
| Fragrance | 1.000 |
| Glyceryl Laurate | 1.000 |
| Hydroxypropylcellulose | 0.550 |
| PEG-40 Hydrogenated castor oil | 0.400 |
| Citric acid | 0.260 |
| Sorbic acid | 0.224 |
| Potassium hydroxide (85%) | 0.132 |
| FD&C Yellow No. 6* | 0.100 |
| FD&C Yellow No. 5* | 0.080 |
|  | 100.000 |

*aqueous solution 0.1%

While the invention has been described in connection with the preferred embodiment, it is not intended to limit the scope of the invention to the particular form set forth, but, on the contrary, it is intended to cover such alternatives, modifications, and equivalents as may be included within the spirit and scope of the invention as defined by the appended claims.

We claim:

1. A deodorant composition comprising about 0.5-5% glyceryl laurate, about 0.1-0.5% sorbic or benzoic acid, and about 0.1-0.5% citric acid in an aqueous-/alcoholic carrier.

2. The composition of claim 1 wherein the aqueous-/alcoholic carrier comprises one or more of solvents, humectants, salts, emollients, solubilizers, fragrance, preservatives, colorants, UV-filters, antioxidants.

3. The composition of claim 2 containing:
20.0–80.0% alcohol
0.1–50.0% water
0.1–40.0% humectant/solvent
0.05–0.5% salt 4. The composition of claim 3 containing:
up to 5.0% fragrance
2.0–10.0% emollient 5. The composition of claim 4 wherein the solvent is ethanol or isopropanol in mixtures with butylene glycol, propylene glycol, hexylene glycol, glycerol, sorbitol, or polyethylene glycols.

6. The composition of claim 5 wherein the emollient is one or more of PPG-11 stearyl ether, PPG-15 stearyl ether, PPG-5 laureth-5, PPG-3 myreth-3, PPG-3 myristyl ether, or other ethoxylated/propoylated fatty alcohol ethers.

7. The composition of claim 6 containing:
40.0–70.0% SD Alcohol 39-C
10.0–40.0% water
5.0–20.0% butylene glycol
3.0–7.0% emollient
0.1–3.0% fragrance
0.5–3.0% glyceryl laurate
0.2–0.4% sorbic acid
0.1–0.25% potassium hydroxide
0.15–0.35% citric acid 8. The composition of claim 7 containing:
45.0–50.0% SD alcohol 39-C
30.0–38.0% purified water
5.0–10.0% butylene glycol
4.0–6.0% emollient
0.1–2.0% fragrance
0.5–1.5% glyceryl laurate
0.2–0.3% sorbic acid
0.1–0.2% potassium hydroxide
0.16–0.26% citric acid 9. The composition of claim 7 wherein the emollient is PPG-5 Laureth 5.

10. The composition of claim 8 wherein the emollient is PPG-5 Laureth 5.

11. The composition of claim % wherein the emollient is PPG-15 stearyl ether.

12. The composition of claim 11 containing:
45.0–50.0% SD alcohol 39-C
30.0–38.0% water
5.0–10.0% butylene glycol
4.0–6.0% PPG-15 stearyl ether
0.1–2.0% fragrance
0.5–1.5% glyceryl laurate
0.2–0.8% PEG-40 hydrogenated castor oil
0.2–0.8% hydroxypropylcellulose
0.16–0.26% citric acid 13. The composition of claim 9 containing:
45.0–50.0% SD alcohol 39-C
30.0–38.0% water
5.0–10.0% butylene glycol
4.0–6.0% PPG-5 Laureth-5
0.1–2.0% fragrance
0.5–1.5% glyceryl laurate
0.2–0.8% hydroxypropylcellulose
0.2–0.8% PEG-40 hydrogenated castor oil
0.16–0.26% citric acid 14. A method of suppressing body odor comprising applying to the bodily area where odor suppression is desired a deodorant composition containing an odor suppressing effective amount of a combination of glyceryl laurate, sorbic or benzoic acid, and citric acid.

15. The method of claim 14 wherein the odor suppressing effective amount is 0.5–5% glyceryl laurate, 0.1–0.5% sorbic acid, and 0.1–0.5% citric acid.

16. The method of claim 15 wherein the deodorant composition is applied from a pump spray container, an aerosol container, a roll-on container, a stick, or a cream.

* * * * *